(12) United States Patent
Weill et al.

(10) Patent No.: US 9,035,250 B2
(45) Date of Patent: May 19, 2015

(54) METHOD FOR EVALUATING THE QUANTITY OF METHANE PRODUCED BY A DAIRY RUMINANT

(75) Inventors: Pierre Weill, Vern sur Seiche (FR); Guillaume Chesneau, Luitre (FR)

(73) Assignee: VALOREX, Combourtille (FR)

( * ) Notice: Subject to any disclaimer, the term of this patent is extended or adjusted under 35 U.S.C. 154(b) by 36 days.

(21) Appl. No.: 13/879,546

(22) PCT Filed: Oct. 11, 2011

(86) PCT No.: PCT/EP2011/067689
§ 371 (c)(1),
(2), (4) Date: Apr. 15, 2013

(87) PCT Pub. No.: WO2012/052314
PCT Pub. Date: Apr. 26, 2012

(65) Prior Publication Data
US 2013/0218477 A1  Aug. 22, 2013

(30) Foreign Application Priority Data
Oct. 21, 2010  (FR) .................................... 10 58624

(51) Int. Cl.
*G01J 5/00*     (2006.01)
*G01N 33/487*   (2006.01)
*G01N 33/04*    (2006.01)

(52) U.S. Cl.
CPC .............. *G01N 33/487* (2013.01); *G01N 33/04* (2013.01)

(58) Field of Classification Search
USPC .................. 250/338.1; 426/2; 73/866; 702/19
See application file for complete search history.

(56) References Cited

U.S. PATENT DOCUMENTS

| 5,265,618    | A  | * | 11/1993 | Zimmerman  | .................. 600/531 |
| 2009/0288606 | A1 | * | 11/2009 | Zimmerman  | .............. 119/51.02 |
| 2011/0081442 | A1 | * | 4/2011  | Weill et al. | ........................ 426/2 |
| 2012/0276058 | A1 | * | 11/2012 | Smith et al. | .................. 424/93.4 |
| 2013/0011384 | A1 | * | 1/2013  | Morgavi et al. | ............... 424/115 |
| 2013/0167617 | A1 | * | 7/2013  | Weill et al. | .................. 73/31.05 |

FOREIGN PATENT DOCUMENTS

WO   2009156453   12/2009

OTHER PUBLICATIONS

Author: H. Soyeurt et al., Title: Estimating Fatty Acid Content in Cow Milk Using Mid-Infrared Spectrometry, Date: 2006, Publisher: J. Dairy Sci. 89:3690-3695 © American Dairy Science Association.*
J. L. Ellis, et al., "Modeling methane production from beef cattle using linear and nonlinear approaches", American Society of Animal Science, vol. 87, pp. 1334-1345, dated 2009.
J. L. Ellis et al., "Evaluation of enteric methane prediction equations for dairy cows used in whole farm models", Global Change biology, vol. 16, pp. 3246-3256, dated 2010.
PCT/EP2011/067689, International Search Report, dated Jan. 26, 2012.

* cited by examiner

*Primary Examiner* — David J Makiya
*Assistant Examiner* — Taeho Jo
(74) *Attorney, Agent, or Firm* — Banner & Witcoff, Ltd.

(57) ABSTRACT

A method involves at least measuring the weight quantity of at least one fatty acid (AG), derived from de novo synthesis, in a sample of milk from said ruminant and evaluating said quantity of methane according to the following formula: $CH4 = a*(\text{de novo AG}) + y*(\text{BH AG}) + z$.

12 Claims, No Drawings

METHOD FOR EVALUATING THE QUANTITY OF METHANE PRODUCED BY A DAIRY RUMINANT

This application is a U.S. National Stage application of co-pending PCT application PCT/EP2011/067689 filed Oct. 11, 2011, which claims the priority of French application 10,586,24, filed Oct. 21, 2010.

The present invention relates to a method for evaluating the quantity of methane produced by a dairy ruminant.

Enteric methane (CH4) is a gas emitted by eructation in ruminants. It forms during the fermentation of feed in the rumen of these animals and represents a loss of energy for the animal. But methane is also a powerful greenhouse gas.

On a global scale, animal husbandry could contribute 18% of the total emissions of greenhouse gases (source FAO, 2006). The CH4 emitted by the enteric fermentations of ruminants represents on its own from 3 to 5% of the totality of global greenhouse gas emissions.

Its lifetime in the atmosphere is only 12 years (compared to 100 years for carbon dioxide), such that the implementation of techniques for reducing emissions of said enteric methane is of the greatest interest.

Reducing the emissions of enteric methane from ruminants thus meets a double objective, namely economic and environmental.

Numerous techniques are henceforth proposed to reduce the emissions of enteric methane from ruminants, and particularly dairy ruminants.

However, the problem of the measurement of the efficiency of these techniques will remain posed as long as a simple method has not been developed, which will enable a routine measurement.

Although the emission of enteric methane is characteristic of the fermentation of ruminants, the quantities of methane per kilogram of milk produced varies considerably as of function of the productivity of the cows, the nature of the feed intake, the ruminal ecosystem, etc.

The data of the scientific literature show in this respect an extremely wide range of variation per kilogram of milk. In fact, from around 7 to 25 grams of methane could be emitted per kilogram of milk produced.

The "methane footprint" of the milk may be defined as the quantity of methane emitted daily by a cow while lactating and divided by the number of kilograms of milk produced per day. It is expressed in grams of methane (CH4) per kilogram of milk.

It is thus interesting to be able to estimate in a reliable manner the emissions of methane of each kilogram of milk as a function of the composition thereof, in order to be able to find then promote animal husbandry techniques that reduce and minimise the methane footprint, in other words the quantity of methane emitted for the production of a kilogram of milk.

The scientific literature describes numerous potential methods for reducing emissions of enteric methane.

Without being exhaustive, the following methods may be noted:
 the increase in productivity (kilograms of milk produced per cow and per day) increases the emissions of methane per cow and per day, but reduces the quantity of methane per liter of milk (the term "cow" is used herein because it is the most widespread dairy ruminant);
 the intake of edible oils, which are not fermented in the rumen;
 the use of toxic substances for certain microbial populations of the rumen: antibiotics, essential oils, vegetal extracts, fatty acids, etc., which increases the use of hydrogen by the propionate route to the detriment of that of methane;
 the use of precursors of propionate (malate, fumarate, etc.) which also favour the propionate route to the detriment of the methane route;
 the combination of said different methods, etc.

The publications that describe these effects use as measurement means:
 a) in vitro techniques: these are not always representative of in vivo,
 b) in vivo techniques over short experimental periods: they do not provide guarantees of maintaining the effects over time. They are always difficult to implement and have experimental limits.

The most widespread are those known as
 "Calorimetric chamber" and
 "SF6 Method", namely
the reading of emissions of methane by weight, after collection of eructed gas samples, in comparison with known quantities of SF6 gas derived from a parameterised diffuser, introduced into the rumen of the animal in vivo.

c) "Laser detector" measurement: this recent technique could make it possible to measure in situ the emissions of methane by laser radiation, but the first publications available (Chagunda & al 2009) do not confer it with great reliability.

d) Predictions from the ingested quantities or the nature of the feed intake: numerous equations are proposed by different authors.

They are imprecise and depend on numerous criteria that are not routinely measurable, or not known in general (such as the ingestion of the cows, the fermentability of the feed, etc.)

e) Predictions from the productivity of cows: the more a cow produces milk, the lower are the emissions of methane per kilogram of milk.

The link with productivity does not integrate the differences linked to the types of feed intake, and an attentive reading of the bibliography demonstrates that at identical productivity level, very considerable differences appear when the emissions of methane are measured with different feed intakes.

In the application FR 0854230 in the name of the present applicant, a reliable and simple method is described which integrates at one and the same time the productivity of the cows and the orientation of the ruminal fermentations according to the stoichiometric relation between fatty acids of the rumen, fatty acids of the milk and methane.

Recent publications (Martin 2008, Chilliard 2009.) confirm this link.

Nevertheless, to implement this measure, it is necessary:
 to know the productivity of the cows
 and to carry out a fatty acids profile of the milk which requires:
  an extraction of the lipids of the milk
  and a gas phase chromatography.

The present invention aims to overcome these difficulties.

Thus, it proposes a method for evaluating the quantity of methane produced by a dairy ruminant, characterised in that it consists in at least measuring the weight quantity of at least one fatty acid (AG), derived from de novo synthesis, in a sample of milk from said ruminant and evaluating said quantity of methane according to the following formula:

$$CH4 = a^*(\text{de novo AG}) + y^*(\text{BH AG}) + z$$

relation wherein:
 "CH4" is the quantity, in grams, of methane produced per kilogram or per liter of milk by said ruminant;

"de novo AG" is the measured quantity in the sample, in grams per kilogram or per liter of milk, of at least said fatty acid, taken alone or in combination with at least the measured quantity of another de novo fatty acid;

"BH AG" is the quantity measured in the sample, in grams per kilogram or per liter of milk, of at least one fatty acid derived from ruminal bio-hydrogenation, taken alone or in combination with at least the measured quantity of another fatty acid derived from ruminal bio-hydrogenation;

a is comprised between −2 and 2 when y is equal to zero, or is comprised between 0.1 and 10 when y is different to zero;

y is comprised between −10 and +10 when a is different to zero, or is comprised between −50 and −0.1 when a is equal to zero;

a and y not being able to be equal to zero simultaneously;

z is comprised between −100 and +100.

Thanks to this method, it is possible to be free of the dairy productivity of the ruminant and to determine said quantity of $CH_4$ by analysis of a simple sample of milk.

Furthermore, according to other advantageous and non-limiting characteristics:

"de novo AG" is selected from the following definitions:
a) quantity of saturated fatty acids (AGS) of 4 to 14 carbon atoms;
b) quantity of saturated fatty acids of 4 to 16 carbon atoms;
c) quantity of C12 and C14 saturated fatty acids;
d) quantity of C4, C6, C8, C10, C12, C14 and C16 saturated fatty acids, taken alone or in combination of least two thereof.

said quantity of methane is given by the following formula:

$$CH_4 = (1.07 \pm 0.5) * \text{Sum of C4 to C14 saturated fatty acids} + (4.8 \pm 3).$$

"BH AG" is selected from the following definitions:
a) quantity of the totality of unsaturated fatty acids (AGI);
b) quantity of the totality of unsaturated fatty acids (AGI) comprising at least 18 carbon atoms;
c) quantity of the totality of unsaturated fatty acids (AGI) comprising at least 18 carbon atoms, with the exception of C18:1 n−9, C18:2n−6 and C18:3n−3 unsaturated fatty acids;
d) quantity of C18 saturated fatty acid (C18:0);
e) quantity of trans fatty acids or of a part thereof.

said quantity of methane is given by the following formula:

$$CH_4 = (1.14 \pm 0.4) * \text{Sum of C4 to C14 saturated fatty acids} - (0.07 \pm 0.3) * [AGI - (C18:1n-9 + C18:2n-6 + C18:3n-3)] + (4.7 \pm 0.5)$$

wherein "AGI−(C18:1 n−9+(C18:2n−6+C18:3n−3)" represents the quantity of the totality of unsaturated fatty acids with the exception of C18:1 n−9, C18:2n−6 and C18:3n−3 acids.

one measures said quantity of fatty acid derived from de novo synthesis, by infrared spectroscopy, preferentially in the mid infra-red.

a) the method is repeated with several samples of milk, known as reference samples;

b) one associates with the measured quantity of $CH_4$ of each reference sample, the infrared absorption spectrum thereof;

c) one records the infrared absorption spectrum of a new sample to be tested;

d) one compares said spectrum with the spectra of the reference samples;

e) one deduces the quantity of $CH_4$ associated with the new sample, by comparison of the spectrum thereof with those of the reference samples.

preferentially, at step d), one carries out said comparison by mathematical and statistical models and, at step e), one uses the evaluation equations obtained by the models of step d).

Other characteristics and advantages of the invention will become clear on reading the detailed description that follows.

Throughout the present application, the following expressions are defined as follows:

"de novo lipogenesis": fatty acid synthesis by the mammary epithelial cells;

"de novo fatty acid": fatty acid comprising 16 carbon atoms or less, synthesised by the mammary epithelial cells;

"BH fatty acid" or "fatty acid derived from ruminal bio-hydrogenation": fatty acid with 18 carbon atoms having undergone at least one hydrogenation during the process of ruminal fermentation. They have zero, one or more unsaturations.

Finally, the term "combined" is taken to mean added or subtracted or multiplied or divided.

1/ Methane and AGV (Volatile Fatty Acids) Relation—Rumen and Methanogenesis

The link between the production of AGV in the rumen and the production of methane is known and has been studied for many years.

Thus, it has been shown that the production of acetate and butyrate in the rumen releases hydrogen and thus favours the production of methane, whereas the production of propionate enables the use of hydrogen and thus limits the production of methane. This may be illustrated by the following formulas:

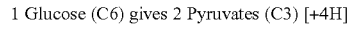
1 Glucose (C6) gives 2 Pyruvates (C3) [+4H]

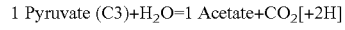
1 Pyruvate (C3)+$H_2O$=1 Acetate+$CO_2$[+2H]

and

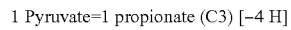
1 Pyruvate=1 propionate (C3) [−4 H]

A prediction equation has thus been developed to predict the production of $CH_4$ from the production of AGV, according to a publication of Moss et al., 2000. Thus, the more the fermentations of the rumen produces C2 (acetate) and C4 (butyrate), the higher the production of $CH_4$.

Conversely, the more the fermentations of the rumen produce C3 (propionate), the lower the production of $CH_4$.

The synthesis equation that ensues from this is defined as follows $$[CH4]=0.45 [\text{acetate}]+0.40 [\text{butyrate}]-0.275 [\text{propionate}] \quad \text{(Moss formula)}$$

where [x]=quantity of x, in % of the total AGV.

The link between the de novo lipogenesis and methanogenesis appears here since C2 and C4 are the precursors of de novo fatty acids (de novo AG) synthesised in the teat.

The more C2 and C4 there are produced by the fermentations of the rumen the more there will be of substrates available for the de novo synthesis of fatty acids of the milk.

2/ Teat and Lipogenesis

The C2 and C4 AGV derived from ruminal fermentations are then taken up by the mammary epithelial cells to serve as substrate to the syntheses of de novo AG.

If the availability of AGV substrates is the factor limiting these syntheses, (which is very generally the case), then there exists a relation of strict proportionality between the emissions of enteric $CH_4$ and the excretions of AG derived from de novo synthesis in the milk, as the table below shows.

| Substrate | de novo AG |
|---|---|
| 2 C2 (or a C4) make | C4:0 |
| 3 C2 | C6:0 |
| 4 C2 | C8:0 |
| 5 C2 | C10:0 |
| 6 C2 | C12:0 |
| 7 C2 | C14:0 |
| 8 C2 | C16:0 |

The synthesis of de novo AG in mammary endothelial cells takes place almost exclusively from C2 and C4 substrates derived from ruminal fermentations with a "methane footprint", as the Moss formula developed above suggests.

It then ends up in the synthesis of the following even saturated fatty acids: C4:0, C6:0, C8:0, C10:0, C12:0, C14:0, C16:0.

It will nevertheless be noted that, in a second phase, certain of said saturated AG (AGS) derived from the de novo synthesis may be desaturated.

It then seems tempting to use the double relation (C2+C4) and CH4 (methane) on the one hand and (C2+C4) as precursors of the synthesis of saturated de novo AG in the teat to predict the quantities of methane emitted from the quantities of de novo AG synthesised.

The lipids of the milk also contain odd saturated AG derived from de novo synthesis which use the even AGV substrates (with positive methane impact), but also from C3, the impact of which on methanogenesis is negative. Thus for odd AG, the link between their weight in the milk and their "methane footprint" will be lower.

However, certain even saturated AG may have an exogenous origin, particularly C16:0 which represents on its own nearly one third of all AG of the milk and which may stem from various origins, for example the mobilisation of the reserves of the adipose tissue or an exogenous vegetable oil (palm oil for example), etc. Thus to construct a reliable relation between the methane fingerprint per kilogram of milk and the weight of AG, it is first necessary to have available a reliable measurement of the weight of de novo in each kilogram of milk.

3/ Estimation of the Quantity of De Novo AG Present in the Milk

The mechanisms of synthesis then of esterification of even saturated AG in the teat comprise numerous communal routes.

Also, it is logical to find strong relations between even saturated AG of the milk. The following table (Moate et al, 2007) gives the statistical relations between even C4 to C16 saturated AG of the milk after a meta-analysis of publications on this theme:

| AG | C4:0 | C6:0 | C8:0 | C10:0 | C12:0 | C14:0 |
|---|---|---|---|---|---|---|
| C4:0 | | | | | | |
| C6:0 | 0.8* | | | | | |
| C8:0 | 0.67* | 0.95* | | | | |
| C10:0 | 0.56* | 0.87* | 0.98* | | | |
| C12:0 | 0.49* | 0.85* | 0.91* | 0.97* | | |
| C14:0 | 0.56* | 0.86* | 0.89* | 0.93* | 0.95* | |
| C16:0 | 0.58* | 0.74* | 0.72* | 0.70* | 0.76* | 0.85* |

($p < 0.05$)

It may clearly be seen that all of these AG being linked together by synthesis routes to a large extent communal, their levels in the milk are highly correlated together.

The fatty acid C16:0 appears less correlated with the AGS with short and mid chain than the other even AG of shorter chain length, perhaps due its partially exogenous origin.

The fatty acid C4:0 also appears less well correlated with the other "de novo" AG, perhaps due to routes of synthesis and of esterification (on the triglycerides of the milk) different to the other AG, perhaps also due to analytical difficulties.

Thus, it appears equivalent to use as marker of novo synthesis with, as C2 and C4 substrate, the sum or the combination of each of said AG.

In a preferential manner, the sum by weight of all the short and medium chain AG (from C4:0 to C14:0) which excludes C16:0 (possibly of exogenous origin) seems to be the most reliable relation.

Nevertheless, any even C4 to C16 AG, taken alone, or any sum or combination of at least two of said AG gives a more or less reliable estimation of the use of C2 and C4 substrates for de novo synthesis, thus for ruminal methanogenesis.

Thus, to determine the quantity of CH4 discharged, in grams per kilogram of milk or per liter of milk, the following equation is used:

$$CH4\ (g/kg) = a*\text{de novo AG} + z$$

de novo AG: by weight (g/kg of milk),
equation wherein a is comprised between −2 and +2 and z comprised between −100 and +100.

The de novo AG may be estimated preferentially by the saturated AG(AGS) content of the milk from 4 to 14 carbon atoms.

This formula under-estimates the quantity of C2 and C4 substrates used for the synthesis of mono unsaturated AG of 4 to 16 carbon atoms after a step of mammary desaturation, but slightly overestimates the share of C2 and C4 in the odd saturated AG.

In a particularly preferred manner, this quantity is estimated according to the equation:

$$CH4\ (g/kg) = 1.07 * \text{Sum of C4 to C14 AGS} + 4.8$$

Wherein the sum of C4 to C16 AGS is expressed in grams per kilogram of milk.

But it would also be possible to use other formulas which would include as variant, instead of the sum of C4 to C14 AGS:
- the sum of all the AGS: this is nevertheless a less precise parameter, because the AGS also contain exogenous AG and C18:0 derived from ruminal bio-hydrogenations.
- the sum of the saturated AG of 4 to 16 carbon atoms: a not always known part of the C16:0 is nevertheless of exogenous origin.
- the sum of C12:0 and C14:0;
- C4:0, C6:0, C8:0, C10:0, C12:0, C14:0, C16:0, taken alone or in combination of at least two thereof.

4/ Gain in Precision

The method according to the invention takes into account well the link between methanogenesis and lipogenesis as described above.

Nevertheless, variations of emissions of methane are here linked to the distribution/competition of hydrogen between the routes for the synthesis of methane and those for the synthesis of propionate.

Yet, routes other than that of methanogens and propionate exist for the use of hydrogen. Most are marginal, but the hydrogen metabolic produced during anaerobic fermentations of the rumen can also be used during hydrogenation reactions of poly-unsaturated AG of the feed intake.

Thus, the equation indicated above may also be written:

$$CH4(g/kg) = a*\text{de novo AG} + y\ BH\ AG* + z$$

BH AG=AG derived from ruminal bio-hydrogenation
Equation wherein:
- a is comprised between −2 and 2 when y is equal to zero, or is comprised between 0.1 and 10 when y is different to zero;
- y is comprised between −10 and +10 when a is different to zero, or is comprised between −50 and −0.1 when a is equal to zero;
- a and y not being able to be equal to zero simultaneously;
- z is comprised between −100 and +100.

The AG derived from bio-hydrogenation represents the sum of all the AG with 18 and more carbon atoms, less those of exogenous origin.

They comprise:
- stearic acid (C18:0), but this may also have an exogenous origin;
- oleic acid (C18:1 n−9) when it is derived from the desaturation in the teat of C18:0, but this can also have an exogenous origin.
- all the AG with more than 2 unsaturations with the exception of linoleic (C18:2 n−6) and alpha-linolenic (C18:3 n−3) acids of exogenous origin.
- it is also advisable to remove the AG:C20:4 n−6, C20:5 n−3, C22:6 n−3, or longer chain length.

Their specific contribution (apart from the general effects of oils on ruminal fermentation apprehended from the de novo AG) to the reduction of methane emissions through competition with the hydrogen is not completely negligible.

By way of example.
- 360 g of dietary C18:1 n−9 (2% of the feed intake), 85% hydrogenated in the rumen "consumes" the hydrogen required for the synthesis of 0.4 g of CH4 per kilogram of milk. 2% of CH4 emissions)
- 360 g of dietary C18:2 n−6, 85% hydrogenated in the rumen "consumes" the hydrogen required for the synthesis of 0.7 g of CH4 per kilogram of milk. 4%)
- 360 g of dietary C18:3 n−3, 85% hydrogenated in the rumen "consumes" the hydrogen required for the synthesis of 1.1 g of CH4 per kilogram of milk. 6%)

The nature of the AG derived from bio-hydrogenation is complex.

Among the AG with 18 carbon atoms and more, certain such as C18:1 n−9 may have an endogenous (hydrogenation in C18:0, then desaturation in C18:1 n−9) or exogenous origin (with rapeseed oils for example).

The value of [AGI−(C18:1 n−9)−(C18:2 n−6)−(C18:3 n−3)] is a good indicator of the quantity of AG derived specifically from hydrogenation.

Thus, the aforementioned equation may advantageously be written:

$$CH4(g/kg)=1.14*(\text{Sum of C4 to C14 AGS})$$
$$0.07*[AGI-(C18:1\ n-9+C18:2\ n-6+C18:3\ n-3)]+4.7$$

It is also possible to use other formulas which would include as variant, instead of AGI−(C18:1 n−9+C18:2 n−6+C18:3 n−3) other indicators of bio-hydrogenation such as
- the sum of AGI;
- the C18:0;
- the sum of trans AG or certain thereof.

As indicated above, the state of the art does not enable a direct, rapid and easy to implement reading. The most precise predictions currently necessitate knowing at least the lipids content of the milk and the productivity of the cows, two factors that are not known routinely.

The present method makes it possible to estimate the emissions of methane per kilogram of milk from a single criterion (and no longer a minimum of three): the content of said milk in one or more fatty acids expressed in grams per kilogram.

5/ Implementation of the Method

For several years, the technique of rapid measurement of the AG of the milk in grams per kilogram of milk (or per liter) by infrared spectroscopy has been developing.

From a data base of milk samples, this consists in linking for each sample of milk, the composition in AG (in grams per liter) obtained by a reference analysis (such as gas phase chromatography) and the light absorption spectrum obtained by infrared analysis. By mathematical and statistical methods making use of equations (or calibrations), from the moment that the level of reliability of the measurement is satisfactory, it then becomes possible to estimate by equations the AG of any sample of milk by infrared analysis, using estimation equations determined beforehand.

Since the stoichiometric link between the AG of the milk and the emission of methane is known, it is tempting to use the direct reading of the AG of the milk in grams per kilogram (or per liter) to evaluate "the methane footprint" of the milk.

There is no longer a need to know the productivity per cow, or the total lipids content of the milk.

The use of infrared spectroscopy, more precisely mid infrared, makes it possible to measure the AG content of samples of liquid milk directly in grams/kilogram of milk (or per liter).

The precision of this method is more and more reliable, as recent publications indicate (Soyeurt et al, 2010).

This advance in the technique enables the present invention to be implemented with great facility.

It is thus no longer necessary to carry out an extraction of the lipids and a gas phase chromatography, or to know the total lipids content of the milk and the productivity of the cows.

According to the invention, the measurement of the methane footprint of each kilogram of milk may be carried out, in a routine manner, at each instant.

Instead of measuring successively the AG, taken alone or in combination, by the infrared spectral analysis of the milk, then the CH4 from these AG, it may also be envisaged to deduce directly the CH4 from the infrared spectral analysis.

In fact, the quantities of de novo AG, at least, are today very well determined in the mid infrared and are specifically linked to identified absorption spectral bands, and the wavelengths of which correspond to their light absorption. It is thus possible to determine directly the CH4 of a sample of milk from a spectral analysis without going through the measurement of the AG of the milk, but by using the same spectral bands.

The invention claimed is:

1. Method for evaluating the quantity of methane produced by a dairy ruminant, comprising measuring the weight quantity of at least one fatty acid (AG), derived from de novo synthesis, in a sample of milk from said ruminant and evaluating said quantity of methane according to the following formula:

$$CH4=a*(\text{de novo AG})+y*(\text{BH AG})+z$$

wherein:
- "CH4" is the quantity, in grams, of methane produced per kilogram or per liter of milk by said ruminant;
- "de novo AG" is the quantity measured in the sample, in grams per kilogram or per liter of milk, of at least said fatty acid, taken alone or in combination with at least the measured quantity of another de novo fatty acid;
- "BH AG" is the measured quantity in the sample, in grams per kilogram or per liter of milk, of at least one fatty acid derived from ruminal bio-hydrogenation, taken alone or in combination with at least the measured quantity of another fatty acid derived from ruminal bio-hydrogenation;

a is between −2 and 2 when y is equal to zero, or is between 0.1 and 10 when y is different to zero;

y is between −10 and +10 when a is different to zero, or is between −50 and −0.1 when a is equal to zero;

a and y not being able to be equal to zero simultaneously;

z is comprised between −100 and +100, and further comprising measuring said quantity of fatty acid derived from de novo synthesis, by infrared spectroscopy.

2. Method according to claim 1, wherein "de novo AG" is selected from the following definitions:
   a) the quantity of saturated fatty acids (AGS) from 4 to 14 carbon atoms;
   b) the quantity of saturated fatty acids from 4 to 16 carbon atoms;
   c) the quantity of C12 and C14 saturated fatty acids;
   d) the quantity of C4, C6, C8, C10, C12, C14 and C16 saturated fatty acids, taken alone or in combination of at least two thereof.

3. Method according to claim 2, wherein y is equal to zero, and wherein said quantity of methane is given by the following formula:

$$CH4=(1.07\pm0.5)*\text{Sum of C4 to C14 saturated fatty acids}+(4.8\pm3).$$

4. Method according to one of claims 1, wherein y is not zero, and wherein "BH AG" is selected from the following definitions:
   a) the quantity of the totality of unsaturated fatty acids (AGI);
   b) the quantity of the totality of unsaturated fatty acids (AGI) comprising at least 18 carbon atoms;
   c) the quantity of the totality of unsaturated fatty acids (AGI) comprising at least 18 carbon atoms, with the exception of C18 : 1n−9, C18:2n−6 and C18:3n−3 unsaturated fatty acids;
   d) the quantity of C18 saturated fatty acid (C18:0);
   e) the quantity of trans fatty acids or a part thereof.

5. Method according to claim 4, wherein said quantity of methane is given by the following formula:

$$CH4=(1.14\pm0.4)*\text{Sum of C4 to C14 saturated fatty acids}-m(0.07\pm0.03)*[AGI-(C18:1\ n-9+C18:2n-6+C18:3n-3)]+(4.7\pm0.5)$$

wherein "AGI−(C18:1n−9+C18:2n−6+C18:3n−3)" represents the quantity of the totality of unsaturated fatty acids with the exception of C18:1 n−9, C18:2n−6 and C18:3n−3 acids.

6. Method for evaluating the quantity of methane produced by a dairy ruminant, comprising measuring the weight quantity of at least one fatty acid (AG), derived from de novo synthesis, in a sample of milk from said ruminant and evaluating said quantity of methane according to the following formula:

$$CH4=a*(\text{de novo AG})+y*(\text{BH AG})+z$$

wherein:
"CH4" is the quantity, in grams, of methane produced per kilogram or per liter of milk by said ruminant;
"de novo AG" is the quantity measured in the sample, in grams per kilogram or per liter of milk, of at least said fatty acid, taken alone or in combination with at least the measured quantity of another de novo fatty acid;
"BH AG" is the measured quantity in the sample, in grams per kilogram or per liter of milk, of at least one fatty acid derived from ruminal bio-hydrogenation, taken alone or in combination with at least the measured quantity of another fatty acid derived from ruminal bio-hydrogenation;

a is between −2 and 2 when y is equal to zero, or is between 0.1 and 10 when a is equal to zero;

y is between −10 and +10 when a is different to zero, or is between −50 and −0.1 when a is equal to zero;

a and y not being able to be equal to zero simultaneously;

z is between −100 and +100 and further comprising
   a) repeating the method with several samples of milk, known as reference samples;
   b) associating with the measured quantity of CH4 of each reference sample, the infrared absorption spectrum thereof;
   c) recording the infrared absorption spectrum of a new sample to test;
   d) comparing said spectrum with the spectra of the reference samples;
   e) deducing the quantity of CH4 associated with the new sample, by comparison of the spectrum thereof with those of the reference samples.

7. Method according to claim 6, wherein, at step d), said spectrum is compared by mathematical and statistical models and, at step e), deducing the quantity of CH4 using evaluation equations obtained by the models of step d).

8. Method according to claim 6, wherein "de novo AG" is selected from the following definitions:
   a) the quantity of saturated fatty acids (AGS) from 4 to 14 carbon atoms;
   b) the quantity of saturated fatty acids from 4 to 16 carbon atoms;
   c) the quantity of C12 and C14 saturated fatty acids;
   d) the quantity of C4, C6, C8, C10, C12, C14 and C16 saturated fatty acids, taken alone or in combination of at least two thereof.

9. Method according to claim 6, wherein y is equal to zero, and wherein said quantity of methane is given by the following formula:

$$CH4=(1.07\pm0.5)*\text{Sum of C4 to C14 saturated fatty acids}+(4.8\pm3).$$

10. Method according to one of claims 6, wherein y is not zero, and wherein "BH AG" is selected from the following definitions:
    a) the quantity of the totality of unsaturated fatty acids (AGI);
    b) the quantity of the totality of unsaturated fatty acids (AGI) comprising at least 18 carbon atoms;
    c) the quantity of the totality of unsaturated fatty acids (AGI) comprising at least 18 carbon atoms, with the exception of C18: 1n−9, C18:2n−6 and C18:3n−3 unsaturated fatty acids;
    d) the quantity of C18 saturated fatty acid (C18:0);
    e) the quantity of trans fatty acids or a part thereof.

11. Method according to claim 10, wherein said quantity of methane is given by the following formula:

$$CH4=(1.14\pm0.4)*\text{Sum of C4 to C14 saturated fatty acids}-m(0.07\pm0.03)*[AGI-(C18:1\ n-9+C18:2n-6+C18:3n-3)]+(4.7\pm0.5)$$

wherein "AGI−(C18:1n−9+C18:2n−6+C18:3n−3)" represents the quantity of the totality of unsaturated fatty acids with the exception of C18:1 n−9, C18:2n−6 and C18:3n−3 acids.

12. Method according to claim 6, further comprising measuring said quantity of fatty acid derived from de novo synthesis, by infrared spectroscopy.

* * * * *